(12) United States Patent
Ueda et al.

(10) Patent No.: US 7,091,373 B2
(45) Date of Patent: Aug. 15, 2006

(54) PRODUCTION METHOD FOR BIARYLALANINE

(75) Inventors: Hiroshi Ueda, Ibaraki (JP); Isao Kurimoto, Suita (JP)

(73) Assignee: Sumitomo Chemical Company, Limited, Osaka (JP)

(*) Notice: Subject to any disclaimer, the term of this patent is extended or adjusted under 35 U.S.C. 154(b) by 154 days.

(21) Appl. No.: 10/377,710

(22) Filed: Mar. 4, 2003

(65) Prior Publication Data

US 2004/0024229 A1    Feb. 5, 2004

(30) Foreign Application Priority Data

Mar. 18, 2002    (JP)    ............... 2002-073833

(51) Int. Cl.
C07C 233/63    (2006.01)
(52) U.S. Cl. ........................................ 560/38; 562/443
(58) Field of Classification Search .................. 560/38; 562/443
See application file for complete search history.

(56) References Cited

FOREIGN PATENT DOCUMENTS

| DE | 199 63 563 A1 | 7/2001 |
|---|---|---|
| EP | 1 127 861 A1 | 8/2001 |
| EP | 1 233 013 A1 | 8/2002 |
| EP | 1 270 582 A1 | 1/2003 |
| WO | WO 95/31461 A1 | 11/1995 |
| WO | WO 00/43372 A1 | 7/2000 |
| WO | WO 00/68237 A1 | 11/2000 |
| WO | WO 01/12183 A1 | 2/2001 |
| WO | WO 01/36376 A1 | 5/2001 |
| WO | WO 01/42368 A1 | 6/2001 |
| WO | WO 01/66248 A2 | 9/2001 |
| WO | WO 01/68657 A1 | 9/2001 |

OTHER PUBLICATIONS

Eguchi et al., "Synthesis of Neoflavenes by a Palladium-Catalyzed Cross-Coupling Reaction of 4-Trifluoromethylsulfonyloxy-2H-Chromenes with Arylboronic Acids", Bull. Chem. So. Jpn., vol. 75, No. 3, 2002, pp. 581-585.
Zim et al., "NiCl$_2$(Pcy$_3$)$_2$: A Simple and Efficient Catalyst Precursor for the Suzuki Cross-Coupling of Aryl Tosylates and Arylboronic Acids", Organic Letters, vol. 3, No. 19, 2001, pp. 3049-3051.
Huffman et al., "Alternatives to Vinyl Triflates for Cross-Coupling with Arylboronic Acids", Synlett, No. 4, 1999, pp. 471-473.
Ueda et al., "Synthesis of Biaryls via Nickel-Catalyzed Cross-Coupling Reaction of Arylboronic Acids and aryl Mesylates", Tetrahedron, vol. 54, 1998, pp. 13079-13086.
Kobayashi et al., "Nickel-Catalyzed Coupling Reaction of Lithium Organoborates and Aryl Mesylates Possessing An Electron Withdrawing Group", Tetrahedron Letters, vol. 37, No. 47, 1996, pp. 8531-8534.

(Continued)

Primary Examiner—Kamal A. Saeed
(74) Attorney, Agent, or Firm—Sughrue Mion, PLLC

(57) ABSTRACT

There is provided a production method for producing a biarylalanine compound of formula (4):

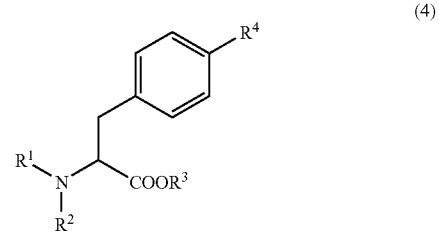

wherein $R^1$ represents a amino protective group and $R^2$ represents an amino protective group or a hydrogen atom, $R^3$ is a carboxy protective group, or the like, and
$R^4$ is a substituted or unsubstituted aryl or heteroaryl group, characterized by reacting an aromatic amino acid of formula (1)

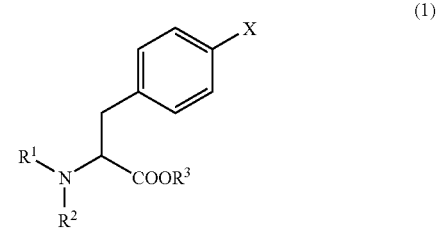

wherein X is a halogen atom or a trifluoromethanesulfonyloxy group, and $R_1$, $R^2$ and $R^3$ has the same meaning as defined above, with an organic boron compound of formula (2):

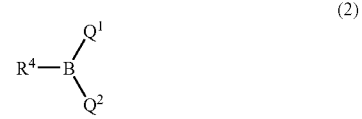

wherein $R^4$ has the same meaning as defined above, and $Q^1$ and $Q^2$ are the same or different and each is a hydroxy group, an alkoxy group having 1 to 4 carbon atom(s), in the presence of nickel catalyst and a base.

17 Claims, No Drawings

OTHER PUBLICATIONS

Percec et al., "Aryl Mesylates in Metal Catalyzed Homocoupling and Cross-Coupling Reactions. 2. Suzuki-Type Nickel-Catalyzed Cross-Coupling of Aryl Arenesulfonates and Aryl Mesylates with Arylboronic Acids", *J. Org. Chem.*, vol. 60, No. 4, 1995, pp. 1060-1065.

F. Firooznia et al., "Synthesis of 4-Substituted Phenylalanines by Cross-Coupling Reactions: Extension of the Methodology to Aryl Chlorides", Tetrahedron Letters, vol. 39, (1998), pp. 3985-3988.

F. Firooznia et al., "Enantioselective Synthesis of 4-Substituted Phenylalanines by Cross-Coupling Reactions", Tetrahedron Letters, vol. 40, No. 2, (Jan. 8, 1999), pp. 213-216.

Y. Satoh et al., Synthesis of 4-Substituted Phenylalanine Derivatives by Cross-Coupling Reaction of $_p$-Boronophenylalanines, Tetrahedron Letters, vol. 38, No. 44, (Nov. 3, 1997), pp. 7645-7648.

J. Galland et al., "Cross-Coupling of Chloroarenes with Boronic Acids using a Water-Soluble Nickel Catalyst", Tetrahedron Letters, vol. 40, No. 12, (Mar. 19, 1999), pp. 2323-2326.

PRODUCTION METHOD FOR BIARYLALANINE

BACKGROUND OF THE INVENTION

1. Field of the Invention

The present invention relates to a production method for a biarylalanine, which is useful as an intermediate for a medicament, an agrochemical and the like.

2. Background of the Invention

As conventional production methods for a biarylalanine compound, the following method are known: a method comprising cross-coupling N-(t-butyloxycarbonyl)-O-(trifluoromethanesulfonyl)tyrosine methyl ester, which is a derivative of a natural amino acid tyrosine, with phenylboronic acid in the presence of a palladium catalyst (WO 2001-36376), a method comprising cross-coupling N-FMOC-4-(trimethylstannyl)-phenylalanine tert-butyl ester with a halobenzene in the presence of a palladium catalyst (WO 2001-12183), a method comprising cross-coupling N-(t-butyloxycarbonyl)-4-iodophenylalanine methyl ester with phenyl boronic acid in the presence of a palladium catalyst (WO 2000-43372) and the like.

However, in each of the above-mentioned cross-coulping methods, an expensive palladium catalyst is used. Therefore, an economical production method has been desired.

SUMMARY OF THE INVENTION

According to the present invention, a biarylalanine compound can be produced economically and in a good yield, by cross-coupling a phenylalanine compound having a halogen group or a trifluoromethanesulfonyloxy group at 4-position, with an organic boron compound, using a nickel catalyst that is more inexpensive than a palladium catalyst.

The present invention provides a production method for producing a biarylalanine compound of formula (4):

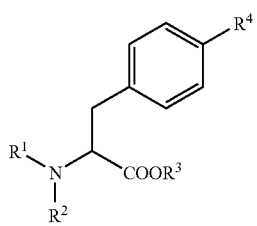

wherein $R^1$ represents amino protective group and $R^2$ represents an amino protective group or a hydrogen atom, $R^3$ is a carboxy protective group, or said amino protective and carboxy protective groups are together to form an amino acid protective group, and $R^4$ is a substituted or unsubstituted aryl or heteroaryl group, which comprises reacting an aromatic amino acid of formula (1):

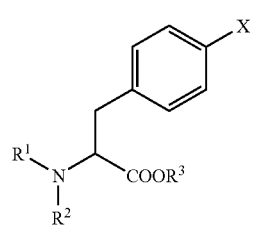

wherein X is a halogen atom, or a trifluoromethylsulfonyloxy group, and $R^1$, $R^2$ and $R^3$ has the same meaning as defined above, with an organic boron compound of formula (2):

wherein $R^4$ has the same meaning as defined above, and $Q^1$ and $Q^2$ are the same or different and independently represents a hydroxy group, an alkoxy group having 1 to 4 carbon atoms, or $Q^1$ and $Q^2$ are together to form an alkylenedioxy group or a 1,2-phenylenedioxy group, each of which is optionally substituted by an alkyl group having 1 to 4 carbon atoms, or a boroxine ring compound of formula (3):

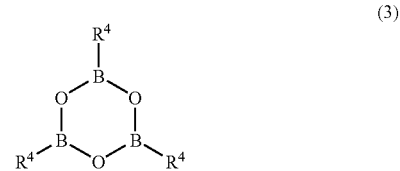

wherein $R^4$ has the same meaning as defined above, or a mixture thereof, in the presence of a nickel catalyst and a base.

DETAILED DESCRIPTION OF THE INVENTION

Hereinafter the present invention is explained in more detail.

Examples of the halogen atom represented by X in formula (1) include, for example, chlorine, bromine, iodine.

Examples of the protective group for $R^1$ and $R^2$ in the aromatic amino acid derivative (1) and the biarylalanine compound (4), include, for example, carbamate protective groups such as methyloxycarbonyl group, ethyloxycarbonyl group, isobutyloxycarbonyl group, t-butyloxycarbonyl group, t-amyloxycarbonyl group, 2,2,2-trichloroethyloxycarbonyl group, 2-trimethylsilylethyloxycarbonyl group, phenylethyloxycarbonyl group, 1-(1-adamantyl)-1-methylethyloxycarbonyl group, 1,1-dimethyl-2-haloethyloxycarbonyl group, 1,1-dimethyl-2,2-dibromoethyloxycarbonyl group, 1,1-dimethyl-2,2,2-trichloroethyloxycarbonyl group, 1-methyl-1-(4-biphenylyl)ethyloxycarbonyl group, 1-(3,5-di-t-butylphenyl)-1-methylethyloxycarbonyl group, 2-(2'-pyridyl)ethyloxycarbonyl group, 2-(4'-pyridyl)ethyloxycarbonyl group, 2-(N,N-dicyclohexylcarboxyamide)ethyloxycarbonyl group, 1-adamantyloxycarbonyl group, vinyloxycarbonyl group, allyloxycarbonyl group, 1-isopropylallyloxycarbonyl group, cynnamyloxycarbonyl group, 4-nitrocynnamyloxycarbonyl group, 8-quinolyloxycarbonyl group, N-piperidinyloxycarbonyl group, alkyldithiocarbonyl group, benzyloxycarbonyl group, p-methoxybenzyloxycarbonyl group, p-nitrobenzyloxycarbonyl group, p-bromobenzyloxycarbonyl group, p-chlorobenzyloxycarbonyl group, 2,4-dichlorobenzyloxycarbonyl group, 4-methylsulfinylbenzyloxycarbonyl group, 9-anthrylmethyloxycarbonyl group, diphenylmethyloxycarbonyl group, 9-fluorenylmethyloxycarbonyl group, 9-(2,7-dibromo)fluorenylmethyloxycarbonyl group, 2,7-di-t-butyl[9-(10,10-dioxo-thioxantyl)]methyloxycarbonyl group, 4-methoxyphenacyloxycarbonyl group, 2-methylthioethyloxycarbonyl group, 2-methylsulfonylethyloxycarbonyl group, 2-(p-toluenesulfonyl)ethyloxycarbonyl group, [2-(1,3-dithianyl)]methyloxycarbonyl group, 4-methylthiophenyloxycarbonyl group, 2,4-dimethylthiophenyloxycarbonyl group, 2-phosphonioethyloxycarbonyl group, 2-triphenylphosphonioisopropyloxycarbonyl group, 1,1-dimethyl-2-cyanoethyloxycarbonyl group, m-chloro-p-acyloxybenzyloxycarbonyl group, p-(dihydroxyboryl)benzyloxycarbonyl group, 5-benzoisooxazolylmethloxycarbonyl group, 2-(trifluoromethyl)-6-chromonylmethyloxycarbonyl group, phenyloxycarbonyl group, m-nitrophenyloxycarbonyl group, 3,5-dimethoxybenzyloxycarbonyl group, o-nitrobenzyloxycarbonyl group, 3,4-dimethoxy-6-nitrobenzyloxycarbonyl group, or phenyl(o-nitrophenyl)methyloxycarbonyl group;

amide protective groups such as formyl group, acetyl group, chloroacetyl group, trichloroacetyl group, trifluoroacetyl group, phenylacetyl group, or benzoyl group;

N-alkyl protective groups such as benzyl group, N-di(4-methoxyphenyl)methyl group, N-5-dibenzosuberyl group, N-triphenylmethyl group, (4-methoxyphenyl)diphenylmethyl group, N-9-phenylfluorenyl group, allyl group, N-[2-(trimethylsilyl)ethoxy]methyl group, or N-3-acetoxypropyl group.

Examples of the carboxy protective group represented by $R^3$ include, for example, methyl group, ethyl group, n-propyl group, isopropyl group, n-butyl group, isobutyl group, s-butyl group, t-butyl group, cyclohexyl group, 9-fluorenylmethyl group, methoxymethyl group, benzyloxymethyl group, pivaloyloxymethyl group, phenylacetoxymethyl group, N-phthalimidemethyl group, benzyl group, α-phenetyl group, triphenylmethyl group, diphenylmethyl group, o-nitrobenzyl group, p-nitrobenzyl group, p-methoxybenzyl group, 2,6-dimethoxybenzyl group. Preferred are the alkyl group having 1 to 4 carbon atoms, a benzyl group.

The amino group and the carboxyl group in formula (1) or (4) may be suitably protected by a single protective group for amino acids, and examples of the groups formed by the amino acid residue of formula (1) or (4) and the amino acid protective group, which may be formed by the amino protective and carboxy protective groups include, for example, 4-substitued-5-oxo-1,3-oxazolidine,
4-substitued-2-methyl-5(4H)-oxazolone,
4-substitued-2,5-oxazolidinedione,
5-substituted-2,4-imidazolidinedione and the like.

The aromatic amino acid compound (1) can be readily synthesized from phenylalanine or tyrosine, which are natural amino acids. The protective groups $R^1$, $R^2$, $R^3$ and the group X can be introduced in any order. Two or more substituents may be introduced by one step.

The introduction methods of amino and carboxy protective groups represented by $R^1$, $R^2$ and $R^3$ respectively include, for example, methods generally used for protecting amino acids and peptide synthesis (for example, the method described in Nobuo Izumiya et al, "Basis and Experiments for Peptide Synthesis", Maruzen Co., Ltd., 1985).

The amino acid protective groups may be suitably introduced by methods as disclosed in "PROTECTIVE GROUPS in ORGANIC SYNTHESIS, 3rd Edition, T. W. Greene and P. G. M. Wuts published by Wiley-Interscience", for example, on pp. 435–436, 503, and 592–595, and the whole disclosures of the references are incorporated herein by reference.

The group X can be introduced by such a method comprising selectively introducing an objective halogen atom at the 4-position of the phenyl group of phenylalanine (a method described in J. Med. Chem., 17(5), 556 (1974)) and the like. Alternatively, the introduction method includes, when X is a trifluoromethanesulfonyloxy group, for example, a method comprising reacting the aromatic hydroxy group of tyrosine with a trifluoromethanesulfonylating agent such as trifluoromethanesulfonic acid anhydride or the like in the presence of a base (Japanese PCT Laid-open Publication No. 2001-521764) and the like.

Specific examples of the aromatic amino acid of formula (1) include, for example, optical isomer or a racemate of:

N-(t-butyloxycarbonyl)-O-trifluoromethanesulfonyltyrosine methyl ester,
N-(t-butyloxycarbonyl)-O-trifluoromethanesulfonyltyrosine ethyl ester,
N-(t-butyloxycarbonyl)-O-trifluoromehanesulfonyltyrosine isopropyl ester,
N-(t-butyloxycarbonyl)-O-trifluoromethanesulfonyltyrosine t-butyl ester,
N-acetyl-O-trifluoromethanesulfonyltyrosine methyl ester,
N-acetyl-O-trifluoromethanesulfonyltyrosine ethyl ester,
N-acetyl-O-trifluoromethanesulfonyltyrosine isopropyl ester,
N-acetyl-O-trifluoromethanesulfonyltyrosine t-butyl ester,
N-acetyl-O-trifluoromethanesulfonyltyrosine benzyl ester,
N-benzyl-O-trifluoromethanesulfonyltyrosine methyl ester,
N-benzyl-O-trifluoromethanesulfonyltyrosine ethyl ester,
N-benzyl-O-trifluoromethanesulfonyltyrosine isopropyl ester,
N-benzyl-O-trifluoromethanesulfonyltyrosine t-butyl ester,
N-benzyl-O-trifluoromethanesulfonyltyrosine benzyl ester,
N-(9-fluorenylmethoxycarbonyl)-O-trifluoromethanesulfonyl-tyrosine methyl ester,
N-(9-fluorenylmethoxycarbonyl)-O-trifluoromethanesulfonyl-tyrosine ethyl ester,
N-(9-fluorenylmethoxycarbonyl)-O-trifluoromethanesulfonyl-tyrosine isopropyl ester,
N-(9-fluorenylmethoxycarbonyl)-O-trifluoromethanesulfonyl-tyrosine t-butyl ester,
N-(9-fluorenylmethoxycarbonyl)-O-trifluoromethanesulfonyl-tyrosine benzyl ester,
N-benzyloxycarbonyl-O-trifluoromethanesulfonyltyrosine methyl ester,
N-benzyloxycarbonyl-O-trifluoromethanesulfonyltyrosine ethyl ester,
N-benzyloxycarbonyl-O-trifluoromethanesulfonyltyrosine isopropyl ester,
N-benzyloxycarbonyl-O-trifluoromethanesulfonyltyrosine t-butyl ester,
N-(t-butyloxycarbonyl-4-chlorophenylalanine methyl ester,
N-(t-butyloxycarbonyl-4-chlorophenylalanine ethyl ester,
N-(t-butyloxycarbonyl-4-chlorophenylalanine isopropyl ester,
N-(t-butyloxycarbonyl-4-chlorophenylalanine t-butyl ester,
N-acetyl-4-chlorophenylalanine methyl ester,
N-acetyl-4-chlorophenylalanine ethyl ester,
N-acetyl-4-chlorophenylalanine isopropyl ester,
N-acetyl-4-chlorophenylalanine t-butyl ester,
N-acetyl-4-chlorophenylalanine benzyl ester,
N-benzyl-4-chlorophenylalanine methyl ester,
N-benzyl-4-chlorophenylalanine ethyl ester,
N-benzyl-4-chlorophenylalanine isopropyl ester, N-benzyl-4-chlorophenylalanine t-butyl ester,
N-benzyl-4-chlorophenylalanine benzyl ester,
N-(9-fluorenylmethoxycarbonyl)-4-chlorophenylalanine methyl ester,
N-(9-fluorenylmethoxycarbonyl)-4-chlorophenylalanine ethyl ester,
N-(9-fluorenylmethoxycarbonyl)-4-chlorophehylalanine isopropyl ester,
N-(9-fluorenylmethoxycarbonyl)-4-chlorophenylalanine t-butyl ester,
N-(9-fluorenylmethoxycarbonyl)-4-chlorophenylalanine benzyl ester,
N-benzyloxycarbonyl-4-chlorophenylalanine methyl ester,
N-benzyloxycarbonyl-4-chlorophenylalanine ethyl ester,
N-benzyloxycarbonyl-4-chlorophenylalanine isopropyl ester,
N-benzyloxycarbonyl-4-chlorophenylalanine t-butyl ester,
N-benzyloxycarbonyl-4-chlorophenylalanine benzyl ester,
N-t-butyloxycarbonyl-4-bromophenylalanine methyl ester,
N-t-butyloxycarbonyl-4-bromophenylalanine ethyl ester,
N-t-butyloxycarbonyl-4-bromophenylalanine isopropyl ester,
N-t-butyloxycarbonyl-4-bromophenylalanine t-butyl ester,
N-t-butyloxycarbonyl-4-bromophenylalanine benzyl ester,
N-acetyl-4-bromophenylalanine methyl ester,
N-acetyl-4-bromophenylalanine ethyl ester,
N-acetyl-4-bromophenylalanine isopropyl ester,
N-acetyl-4-bromophenylalanine t-butyl ester,
N-acetyl-4-bromophenylalanine benzyl ester,
N-benzyl-4-bromophenylalanine methyl ester,
N-benzyl-4-bromophenylalanine ethyl ester,
N-benzyl-4-bromophenylalanine isopropyl ester,
N-benzyl-4-bromophenylalanine t-butyl ester,
N-benzyl-4-bromophenylalanine benzyl ester,
N-(9-fluorenylmethoxycarbonyl)-4-bromophenylalanine methyl ester,
N-(9-fluorenylmethoxycarbonyl)-4-bromophenylalanine ethyl ester,
N-(9-fluorenylmethoxycarbonyl)-4-bromophenylalanine isopropyl ester,
N-(9-fluorenylmethoxycarbonyl)-4-bromophenylalanine t-butyl ester,
N-(9-fluorenylmethoxycarbonyl)-4-bromophenylalanine benzyl ester,
N-benzyloxycarbonyl-4-bromophenylalanine methyl ester,
N-benzyloxycarbonyl-4-bromophenylalanine ethyl ester,
N-benzyloxycarbonyl-4-bromophenylalanine isopropyl ester,
N-benzyloxycarbonyl-4-bromophenylalanine t-butyl ester,
N-benzyloxycarbonyl-4-bromophenylalanine benzyl ester,
N-t-butyloxycarbonyl-4-iodophenylalanine methyl ester,
N-t-butyloxycarbonyl-4-iodophenylalanine ethyl ester,
N-t-butyloxycarbonyl-4-iodophenylalanine isopropyl ester,
N-t-butyloxycarbonyl-4-iodophenylalanine t-butyl ester,
N-t-butyloxycarbonyl-4-iodophenylalanine benzyl ester,
N-acetyl-4-iodophenylalanine methyl ester,
N-acetyl-4-iodophenylalanine ethyl ester,
N-acetyl-4-iodophenylalanine isopropyl ester,
N-acetyl-4-iodophenylalanine t-butyl ester,
N-acetyl-4-iodophenylalanine benzyl ester,
N-benzyl-4-iodophenylalanine methyl ester,
N-benzyl-4-iodophenylalanine ethyl ester,
N-benzyl-4-iodophenylalanine isopropyl ester,
N-benzyl-4-iodophenylalanine t-butyl ester,
N-benzyl-4-iodophenylalanine benzyl ester,
N-(9-fluorenylmethoxycarbonyl)-4-iodophenylalanine methyl ester,
N-(9-fluorenylmethoxycarbonyl)-4-iodophenylalanine ethyl ester,
N-(9-fluorenylmethoxycarbonyl)-4-iodophenylalanine isopropyl ester,
N-(9-fluorenylmethoxycarbonyl)-4-iodophenylalanine t-butyl ester,
N-(9-fluorenylmethoxycarbonyl)-4-iodophenylalanine benzyl ester,
N-benzyloxycarbonyl-4-iodophenylalanine methyl ester,
N-benzyloxycarbonyl-4-iodophenylalanine ethyl ester,
N-benzyloxycarbonyl-4-iodophenylalanine isopropyl ester,
N-benzyloxycarbonyl-4-iodophenylalanine t-butyl ester,
N-benzyloxycarbonyl-4-iodophenylalanine benzyl ester,
and the like.

The organic boron compound (2) and boroxine compound (3), the aryl group for $R^4$ includes, and is not limited to, aryl group having 6 to 14 carbon atoms and consisting of 1 to 3 ring(s) and the like, and such aryl group includes, for example, phenyl group, naphthyl group, anthracenyl group, phenanthryl group, indenyl group, fluorenyl group and the like. The heteroaryl group includes, and is not limited to, a 5- to 7-membered aromatic heterocycle comprising 1 to 3 heteroatom(s) selected from up to 3 nitrogen atoms (i.e. 0, 1, 2 or 3), up to 2 oxygen atoms (i.e. 0, 1 or 2) and up to 2 sulfur atoms(i.e. 0, 1 or 2), and such heteroaryl group includes, for example, pyridyl group, furyl group, thienyl group, pyrrolyl group, imidazolyl group and the like.

Examples of the substituent groups of the substituted aryl or heteroaryl group represented by $R^4$ include, for example, fluorine atom, alkyl groups such as methyl group, ethyl group, i-propyl group, or cycloalkyl group, haloalkyl groups such as trifluoromethyl group, dialkylaminoalkyl group such as N,N-dimethylaminomethyl group, hydroxyl group, alkoxy groups such asmethoxy group, ethoxy group, t-butoxygroup, phenoxy group, mercapto group, alkylthio groups such as methylthio, arylthio groups such as phenylthio group, cyano group, nitro group, amino group, substituted amino groups such as dimethylamino group, cyclohexylamino group and the like, acylamino groups such as t-butoxycarbonyl amino group, acetoxyamino group, sulfoneamide groups such as benzenesulfoneamide group, methanesulfonylamide group, imino group, imide groups such as phthalimide group, formyl group, carboxy group, alkoxycarbonyl groups such as methoxycarbonyl group, aryloxycarbonyl groups such as p-methoxyphenoxycarbonyl group, unsubstituted or substituted carbamoyl groups such as carbamoyl group, N-phenylcarbamoyl group, heterocyclic groups such as pyridyl group, furyl group, thienyl group, aryl groups such as phenyl group ornaphthyl group.

Alternatively, two substituents on the adjacent two carbon atoms of the substituted aryl or heteroaryl group and the aryl or heteroaryl are together to form a fused ring (e.g, methylenedioxyphenyl, indolinyl or the like). These substituents may further be substituted.

Specific examples of the organic boron compound of formula (2) include, phenylboronic acid, 2-methylphenylboronic acid, 3-methylphenylboronic acid, 4-methylphenylboronic acid, 2,3-dimethylphenylboronic acid, 2,4-dimethylphenylboronic acid, 2,5-dimethylphenylboronic acid, 2,6-dimethylphenylboronic acid, 2,4,6-trimethylphenylboronic acid, 2,3,5,6-tetramethylphenylboronic acid, 2-ethyiphenylboronic acid, 4-n-propylphenylboronic acid, 4-isopropylphenylboronic acid, 4-n-butylphenylboronic acid, 4-t-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluorophenylboronic acid, 3,5-bis(trifluoromethyl)phenylboronic acid, 2-methoxyphenylboronic acid, 3-methoxyphenylboronic acid, 4-methoxyphenylboronic acid, 2,5-dimethoxyphenylboronic acid, 2,6-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 4-phenoxyboronic acid, 3,4-methylenedioxyboronic acid, 2-fluorophenylboronic acid, 3-fluorophenylboronic acid, 4-fluorophenylboronic acid, 2,4-difluorophenylboronic acid, 2,5-difluorophenylboronic acid, 2,6-difluorophenylboronic acid, 4,5-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-dimethylaminomethyl)phenylboronic acid, furan-2-boronic acid, furan-3-boronic acid, 2-formylfuranboronic acid, 3-formylfuran-2-boronic acid, dibenzofuran-4-boronic acid, benzofuran-2-boronic acid, thiophene-2-boronic acid, thiophene-3-boronic acid, 5-methylthiophene-2-boronic acid, 5-chlorothiophene-2-boronic acid, 4-methylthiophene-2-boronic acid, 5-methylthiophene-2-boronic acid, 2-acetylthiophene-5-boronic acid, 3-formylthiophene-2-boronic acid, 5-methylthiophene-2-boronic acid, benzothiophene-2-boronic acid, dibenzothiophehe-4-boronicacid, pyrazole-4-boronicacid, 3-methylpyrazole-4-boronic acid, 3,5-dimethylpyrazole-4-boronic acid, 3-nitro-1,2,4-triazole-5-boronic acid, thiazole-2-boronic acid, pyridine-3-boronic acid, pyridine-4-boronic acid, pyrimidine-5-boronic acid, quinoline-8-boronic acid, isoquinoline-4-boronic acid, 1,4-benzenebis(boronic acid), and a pinacol ester, a cathecol ester, a boroxine ring compound thereof, and the like.

The amount of the organic boron compound of formula (2) to be used in the reaction is generally from not less than 1 mol to not more than 10 moles, preferably not more than 3 moles per mol of the aromatic amino acid of formula (1).

The nickel catalyst to be used may be zerovalent or divalent, or the divalent catalyst may be reduced to zerovalent with a reduction agent prior to use. The zerovalent catalyst includes, for example, bis(1,5-cyclooctadiene) nickel (0), tetrakis(triphenylphosphine)nickel (0) and the like. The divalent catalyst includes, for example, metal halides (II) such as nickel chloride (II), nickel bromide (II), nickel iodide (II) and the like, nickel nitrate (II), nickel acetate (II), dichlorobis(triphenylphosphine)nickel (II), bisacetylacetonate nickel (II) and the like. These nickel catalysts may optionally contain a ligand, or the ligand may be added to the reaction mixture. Such ligand includes, for example, triphenylphosphine, tricyclohexylphosphine, tri-tert-butylphosphine, bis(diphenylphosphino)ferrocene and the like.

Examples of the reduction agent that may be used in the reduction of the divalent nickel into the zerovalent nickel prior to use includes, and is not limited to, for example, sodium borohydride, lithium aluminum hydride, sodium hydride, diisobutylaluminum hydride, alkyl Grignard's agent, alkyl lithium, alkyl aluminum, zinc metal and the like. In this case, during the preparation of the catalyst, the divalent catalyst, ligand, reduction agent and optionally a suitable inert solvent are added, and the order of addition is not specifically limited.

The nickel catalyst may be dissolved completely in the reaction mixture, or may be suspended therein. The nickel catalyst may be used as it is, or may be carried onto a substance that can not be dissolved into the solvent to be used for the reaction, such as carbon, silica, alumina or the like.

The amount of the nickel catalyst to be used in the reaction is generally catalytic, preferably from not less than 0.00001 mole to not more than 1 mol, and more preferably not more than 0.2 mol per mol of the aromatic amino acid compound of formula (1). The amount of the ligand to be used is generally not less than 0.1 mol to not more than 10 moles, preferably from not less than 0.5 mol to not more than 5 moles per mol of the nickel catalyst.

A base is generally used in this reaction, and such base includes, for example, a hydroxide, a carbonate, a hydrogencarbonate, a phosphorate, a carboxylate, and an alkoxide of an alkali metal or an alkaline earth metal, an alkali metal fluoride or a tertiary amine.

Such alkali metal salt and alkaline earth metal salt include, for example, sodium hydroxides potassium hydroxides barium hydroxides lithium carbonate, sodium carbonate, potassium carbonate, cesium carbonate, calcium carbonate, barium carbonate, lithium phosphorate, sodium phosphorate, potassium phosphorate and the like.

Examples of the alkali metal fluoride include,for example, Sodium fluorides, potassium fluoride, cesium fluoride and the like.

Examples of the tertiary amine include, for example, trimethylamine, triethylamine, N,N-dimethylbenzylamine, N,N-diehtylaniline and the like.

The amount of the base to be used is generally from 0.1 to 20 moles, preferably from 1 to 5 moles per mol of the aromatic amino acid of formula (1). Furthermore, two or more of the bases may be used in combination.

A solvent is generally used in the reaction, for example, an organic solvent, water, or a mixture thereof may be used as the solvent.

The organic solvent includes, alcohol solvents such as methanol, ethanol and the like, aprotic organic polar solvents such as N-methylpyrrolidone, N,N-dimethylformamide, dimethylsulfoxide, acetonitrile and the like, ether solvents such as diethyl ether, diisopropyl ether, diethylene glycol dimethyl ether, 1,4-dioxane, tetrahydrofuran and the like, aromatic hydrocarbons such as benzene, toluene, xylene and the like, aliphatic hydrocarbons such as hexane, heptane and the like. Each of the solvents is used solely, or two or more of the solvents are used in combination. The amount to be used is generally from not less than 0.5 part by weight to not more than 200 parts by weight, preferably from not less than 1 part by weight to not more than 10 parts by weight per 1 part by weight of the aromatic amino acid compound of formula (1).

In the production method of the present invention, the aromatic amino acid of formula (1), the organic boron compound of formula (2), nickel catalyst, and base, and optionally a ligand and a suitable solvent, may be added in any order. However, when a reduction agent that may react with the aromatic amino acid compound or the organic boron compound is used, preferably these compounds and agents are added in a different order so that undesirable contact can be avoided. For example, a method comprising adding a mixture of a nickel catalyst, a ligand and a reduction agent to a system in which the aromatic amino acid derivative, the organic boron compound and base, and optionally a suitable solvent have been added in any order previously, or a method comprising adding the aromatic amino acid derivative, the organic boron compound and the base and optionally a suitable solvent in any order to a mixture of a nickel catalyst, a ligand and a reduction agent, is preferred. In this case, a nickel catalyst with which a ligand is coodinated may be used instead of the ligand and nickel catalyst.

The reaction is generally carried out under heating, and the reaction temperature is from ambient temperature to the boiling point of the solvent to be used, preferably not more than 70° C.

After the reaction has been completed, the objective biarylalanine compound of the formula (4) can be obtained, by optionally removing the insoluble fraction in the reaction system by filtration and the like and followed by conventional after-treatment(s).

Examples of the biarylalanine compound of formula (4) include, for example,
N-(t-butyloxycarbonyl)-4-phenyl-L-phenylalanine methyl ester,
N-(t-butyloxycarbonyl)-4-phenyl-L-phenylalanine benzyl ester,N-acetyl-4-phenyl-L-phenylalanine methyl ester,
N-(t-butyloxycarbonyl)-4-(2,6-dimethoxyphenyl)-L-phenylalanine methyl ester,
N-(t-butyloxycarbonyl)-4-(2-methoxyphenyl)-L-phenylalanine methyl ester,
N-(t-butyloxycarbonyl)-4-(4-methylphenyl)-L-phenylalanine methyl ester,
N-(t-butyloxycarbonyl)-4-(1-naphthyl)-L-phenylalanine methyl ester,
N-(t-butyloxycarbonyl)-4-(thiophen-2-yl)-L-phenylalanine methyl ester,
N-(t-butyloxycarbonyl)-4-(4-acetylphenyl)-L-phenylalanine methyl ester and racemic compounds of the above-described optically active compounds.

According to the method of the present invention, a biarylalanine, which is useful as a production intermediate for a medicament, an agrochemical and the like, can be obtained economically and in a good yield.

EXAMPLES

Hereinafter the present invention is explained in more detail with referring to the Examples, and the present invention is not limited to these Examples.

Example 1

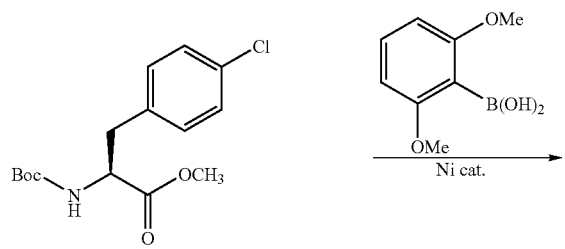

-continued

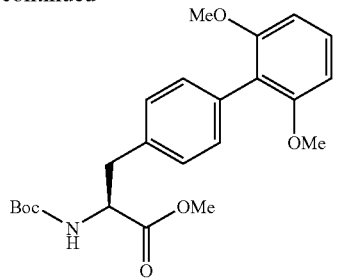

Under nitrogen atmosphere, N-(t-butyloxycarbonyl)-4-chloro-L-tyrosine methyl ester (1.26 g, 4.0 mmol), 2,6-dimethoxyphenylboronicacid (1.09 g, 6.0 mmol), cesium carbonate (2.61 g, 8.0 mmol), tricyclohexylphosphine (0.12 g, 0.4 mmol) and bis(1,5-cyclooctadiene)nickel (0.055 g, 0.2 mmol) were mixed in dioxane (4 ml). The reaction mixture was then heated to 50° C. and stirred at the same temperature for 5 hr. After the reaction had been completed, the reaction mixture was left standing and cooled to room temperature, and insolubles were filtered off. The filtrate was analyzed by liquid chromatography and it was revealed that N-(t-butyloxycarbonyl)-4-(2,6-dimethoxyphenyl)-L-phenylalanine methyl ester was obtained in a yield of 78%.

Example 2

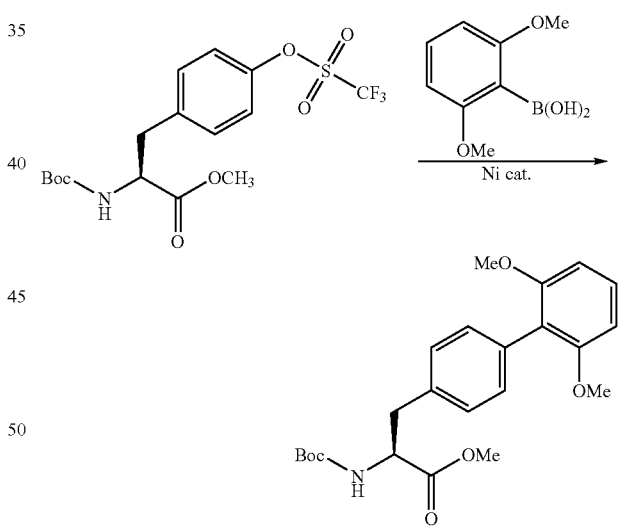

Under nitrogen atmosphere, N-(t-butyloxycarbonyl)-O-(trifluoromethylsulfonyl)-L-tyrosine methyl ester (0.86 g, 2.0 mmol), 2,6-dimethoxyphenyl boronic acid (0.55 g, 3.0 mmol), cesium carbonate (1.30 g, 4.0 mmol), tricyclohexylphosphine (0.24 g, 0.8 mmol) and bis(1,5-cyclooctadiene) nickel (0.056 g, 0.2 mmol) were mixed in dioxane (2 ml). The reaction mixture was then heated to 50° C. and stirred at the same temperature for 5 hr. After the reaction had been completed, the reaction mixture was left standing and cooled to room temperature, and insolubles were filtered off. The filtrate was analyzed by liquid chromatography and it was revealed that N-(t-butyloxycarbonyl)-4-(2,6-dimethoxyphenyl)-L-phenylalanine methyl ester was obtained in a yield of 94%.

What is claimed is:

1. A production method for a biarylalanine compound of formula (4):

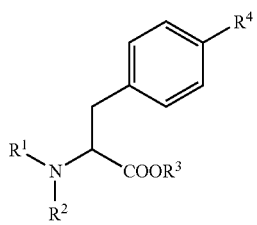

(4)

wherein $R^1$ represents an amino protective group, and $R^2$ represents an amino protective group or a hydrogen atom,
$R^3$ is a carboxy protective group, or said amino protective and carboxy protective groups are together to form an amino acid protective group and
$R^4$ is a substituted or unsubstituted aryl or heteroaryl group, which comprises reacting an aromatic amino acid of formula (1):

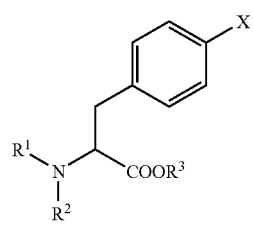

(1)

wherein X is a chlorine atom or a trifluoromethanesulfonyloxy group,
$R^1$, $R^2$ and $R^3$ are the same as defined above, with an organic boron compound of formula (2):

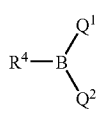

(2)

wherein $R^4$ has the same meaning as defined above, and
$Q^1$ and $Q^2$ are the same or different and independently represent a hydroxy group, an alkoxy group having 1 to 4 carbon atoms, or
$Q^1$ and $Q^2$ are together to form an alkylenedioxy or 1,2-phenylenedioxy group optionally substituted by an alkyl group having 1 to 4 carbon atom or atoms, or
a boroxine ring compound of formula (3):

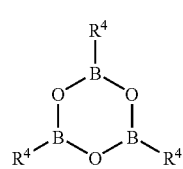

(3)

wherein $R^4$ has the same meaning as defined above, or a mixture thereof, in the presence of a nickel catalyst and a base.

2. The method according to claim 1, wherein X is a halogen atom or trifluoromethanesulfonyloxy group.

3. The method according to claim 1 or 2, wherein the amino protective group represented by $R^1$ is a carbamate aminoprotective group, an amide amino protective group or an N-alkyl type amino protective group, and $R^2$ is a hydrogen atom.

4. The method according to claim 1 or 2, wherein $R^3$ is an alkyl group having 1 to 4 carbon atoms or a benzyl group.

5. The method according to claim 1 or 2, wherein a nickel catalyst and a ligand are used.

6. The method according to claim 1 or 2, wherein the base is an alkali metal hydroxide, an alkaline earth metal hydroxide, an alkali metal carbonate, an alkaline earth metal carbonate, an alkali metal hydrogencarbonate, an alkali metal alkoxide, an alkaline earth metal alkoxide, an alkali metal fluoride, a tertiary amine, or a mixture thereof.

7. The method according to claim 1 or 2, wherein each of the aromatic amino acid of formula (1) and the biarylalanine of formula (4) are optically active compounds.

8. The method according to claim 3, wherein $R^3$ is an alkyl group having 1 to 4 carbon atoms or a benzyl group.

9. The method according to claim 3, wherein a nickel catalyst and a ligand are used.

10. The method according to claim 4, wherein a nickel catalyst and a ligand are used.

11. The method according to claim 3, wherein the base is an alkali metal hydroxide, an alkaline earth metal hydroxide, an alkali metal carbonate, an alkaline earth metal carbonate, an alkali metal hydrogencarbonate, an alkali metal alkoxide, an alkaline earth metal alkoxide, an alkali metal fluoride, a tertiary amine, or a mixture thereof.

12. The method according to claim 4, wherein the base is an alkali metal hydroxide, an alkaline earth metal hydroxide, an alkali metal carbonate, an alkaline earth metal carbonate, an alkali metal hydrogencarbonate, an alkali metal alkoxide, an alkaline earth metal alkoxide, an alkali metal fluoride, a tertiary amine, or a mixture thereof.

13. The method according to claim 5, wherein the base is an alkali metal hydroxide, an alkaline earth metal hydroxide, an alkali metal carbonate, an alkaline earth metal carbonate, an alkali metal hydrogencarbonate, an alkali metal alkoxide, an alkaline earth metal alkoxide, an alkali metal fluoride, a tertiary amine, or a mixture thereof.

14. The method according to claim 3, wherein each of the aromatic amino acid of formula (1) and the biarylalanine of formula (4) are optically active compounds.

15. The method according to claim 4, wherein each of the aromatic amino acid of formula (1) and the biarylalanine of formula (4) are optically active compounds.

16. The method according to claim 5, wherein each of the aromatic amino acid of formula (1) and the biarylalanine of formula (4) are optically active compounds.

17. The method according to claim 6, wherein each of the aromatic amino acid of formula (1) and the biarylalanine of formula (4) are optically active compounds.

* * * * *